US00PP26169P3

(12) United States Plant Patent
Meilland

(10) Patent No.: US PP26,169 P3
(45) Date of Patent: Dec. 1, 2015

(54) GRANDIFLORA ROSE PLANT NAMED 'MEILANTMEN'

(50) Latin Name: *Rosa hybrida/Grandiflora Rose Plant*
Varietal Denomination: Meilantmen

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 31 days.

(21) Appl. No.: 13/987,542

(22) Filed: Aug. 6, 2013

(65) Prior Publication Data

US 2015/0047082 P1 Feb. 12, 2015

(51) Int. Cl.
*A01H 5/02* (2006.01)

(52) U.S. Cl.
USPC ..... Plt./130
CPC ..... *A01H 5/0222* (2013.01)

(58) Field of Classification Search
USPC ..... Plt./130
CPC ..... A01H 5/0222
See application file for complete search history.

*Primary Examiner* — Keith O. Robinson
(74) *Attorney, Agent, or Firm* — Buchanan, Ingersoll & Rooney PC

(57) ABSTRACT

A new and distinct variety of Grandiflora rose plant is provided that abundantly and substantially continuously forms attractive very double cup-shaped multi-colored blossoms having a medium fragrance. The vegetation is very strong. A semi-erect growth habit is displayed. The foliage is dense dark green with a glossy upper surface. The tolerance to disease is good, with a light sensitivity to black spot having been observed during observations to date. The plant is well suited for providing distinctive colorful ornamentation in the landscape.

1 Drawing Sheet

Botanical/commercial classification: *Rosa hybrida*/Grandiflora Rose Plant.

Varietal denomination: cv. Meilantmen.

SUMMARY OF THE INVENTION

The new variety of *Rosa hybrida* Grandiflora rose plant was created in France by artificial pollination wherein two parents were crossed which previously had been studied in the hope that they would contribute the desired characteristics. The female parent (i.e., the seed parent) was the 'Jacnepal' variety (U.S. Plant Pat. No. 11,691). The male parent (i.e., pollen parent) was the 'Meinomad' variety (U.S. Plant Pat. No. 8,248).

The parentage of the new variety can be summarized as follows:

'Jacnepal'×'Meinomad'.

The seeds resulting from the above pollination were sown and small plants were obtained which were physically and biologically different from each other. Selective study resulted in the identification of a single plant of the new variety.

It was found that the new Grandiflora rose plant of the present invention:

(a) forms very strong vegetation,
(b) exhibits a semi-erect growth habit with dense dark green foliage having a glossy upper surface,
(c) abundantly and substantially continuously forms attractive very double multi-colored cup-shaped blossoms having a medium fragrance,
(d) grows well on its own roots, and
(e) is well suited for providing distinctive colorful ornamentation in the landscape.

The tolerance to disease is good with a light sensitivity to black spot having been observed during observations to date. The plant grows well on its own roots.

The new variety well meets the needs of the horticultural industry and can be grown to advantage as colorful ornamentation in parks and gardens.

The new variety can be readily distinguished from its ancestors upon an inspection of the blossoms. More specifically, the 'Jacnepal' variety female parent is a Hybrid Tea that forms orange-white blossoms with red petal edges. The 'Meinomad' variety male parent is a Hybrid Tea rose that forms yellow blossoms suffused with red coloration.

The new variety also can be readily distinguished from the 'Meilampario' variety (non-patented in the United States) and the 'Baipeace' variety (U.S. Plant Pat. No. 14,731). For instance, the blossoms of the 'Meilampario' variety include more yellow coloration at the center, and the blossoms of the 'Baipeace' variety include more ochre coloration.

The new variety has been found to undergo asexual propagation at Le Cannet des Maures, Var, France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meilantmen'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately two years of age and were observed during October while budded on *Rosa laxa* rootstock and growing outdoors at Le Cannet des Maures, Var, France.

DETAILED BOTANICAL DESCRIPTION

Figures 1, 2, 3, 4, 5, 6, 7, 8, 9, 10, 11, 12, 13, 14, 15:
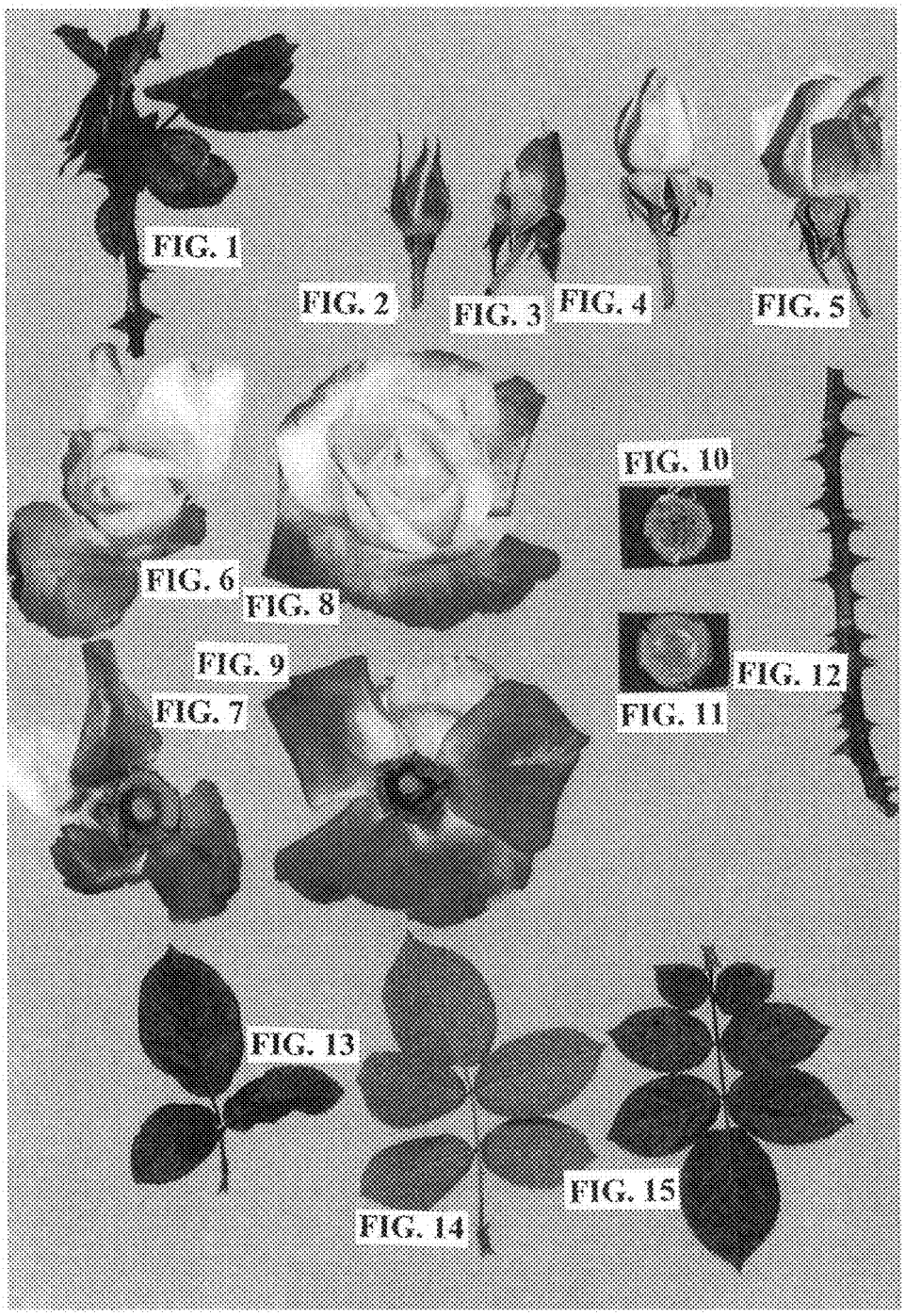
FIG. 1 illustrates a specimen of a young shoot.
FIG. 2 illustrates a specimen of a floral bud at the opening of the sepals.
FIG. 3 illustrates a specimen of a floral bud at the further opening of the sepals and the initiation of some petal opening.
FIG. 4 illustrates a specimen of a floral bud at the further opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a flowering stem.
FIG. 13 illustrates a specimen of a leaf with 3 leaflets—plan view—upper surface.
FIG. 14 illustrates a specimen of a leaf with 5 leaflets—plan view—under surface.
FIG. 15 illustrates a specimen of a leaf with 7 leaflets—plan view—upper surface.

The chart used in the identification of the colors is that of The Royal Horticultural Society (R.H.S. Colour Chart—1995 or equivalent) except where ordinary color terms are utilized. Common color terms are to be accorded their customary dictionary significance. The description is based upon the observation of plants of the new variety at an age of approximately two years during the month of May while being grown outdoors while budded on *Rosa laxa* rootstock at Le Cannet des Maures, Var, France.

Class: Grandiflora.

Plant:

*Growth habit*.—Semi-erect.

*Height*.—Commonly approximately 90 to 100 cm on average.

*Width*.—Commonly approximately 60 to 70 cm on average.

Branches:

*Color*.—Young stems: commonly near Yellow-Green Group 146B and 146C. Adult wood: commonly near Yellow-Green Group 147B.

*Small thorns*.—Configuration: upright on the upper surface and slightly concave on the under surface. Size: commonly approximately 1 to 2 mm in length on average with an oval base on young stems, and commonly 1 to 2 mm in length on average with an obovate base on adult stems. Quantity: commonly approximately 37 on average over a length of 10 cm on young stems, and commonly approximately 54 on average over a length of 10 cm on adult stems. Color: commonly near Greyed-Red Group 179B on young stems, and near Greyed-Orange Group 173C on adult stems.

*Long thorns*.—Configuration: slightly curved downwards on the upper surface and concave on the under surface. Size: commonly approximately 1.2 cm in length on average with an oval base on young stems, and commonly 1 to 1.2 cm in length on average with an obovate base on adult stems. Quantity: commonly approximately 12 on average over a length of 10 cm on young stems, and commonly approximately 21 on average over a length of 10 cm on adult stems. Color: commonly near Greyed-Orange Group 166B on young stems, and near Greyed-Orange Group 173C on adult stems.

Leaves:

*Overall appearance*.—Dense dark green.

*Leaflets*.—Shape: generally oval. Number: 3, most often 5, and 7.

*Size*.—Terminal leaflets commonly are approximately 4.5 cm in length on average and approximately 4 cm in width on average.

*Shape*.—Generally oval and generally without substantial reflexing. Apex: generally acuminate. Base: obtuse. Serration: slightly denticulate, small and single. Texture: firm, and leathery on the under surface, and glossy on the upper surface. Color (young foliage): near Green Group 137B on the upper surface, and near Yellow-Green Group 148B on the under surface. Color (adult foliage): near Yellow-Green Group 147B on the upper surface, and near Yellow-Green Group 147A on the under surface.

*Petiole*.—Length: commonly approximately 3 cm on average. Texture: non-glandular on the upper surface and commonly with many prickles on the under surface. Color: Yellow-Green Group 147B on the upper surface, and near Yellow-Green Group 146C on the under surface.

*Rachis*.—Color: near Yellow-Green Group 146B on the upper surface, and near Yellow-Green Group 146A on the under surface. Texture: non-glandular on the upper surface, and commonly with numerous prickles on the under surface.

*Stipules*.—General appearance: adnate, pectinate, and rather broad. Size: commonly approximately 1.4 cm in length on average, and approximately 7 mm in width on average. Texture: somewhat rough on the upper and under surfaces. Color: near Yellow-Green Group 146B on the upper surface, and near Yellow-Green Group 146A on the under surface.

Inflorescence:

*Number of flowers*.—Commonly approximately 1 to 5 blossoms per stem.

*Buds*.—Shape: generally conical and medium in size. Length: approximately 3 to 3.2 cm on average. Width: approximately 2.7 cm at the widest point on average. Texture: consistent petals. Color: as the calyx breaks: on the upper surface inner petals commonly are near Yellow Group 10D to Yellow Group 11D, and the external petals commonly are near Yellow Group 10D to Yellow Group 11D suffused and edged with near Red Group 42B and 42C and Orange-Red Group 33A, with a spot of near Yellow Group 9A at the base, and on the under surface near Yellow Group 10D to Yellow Group 11D suffused with near Red Group 42B and 42C and near Orange-Red Group 33A, with a spot of near Yellow Group 9A at the base.

*Flower*.—Diameter: approximately 11 to 12 cm on average when fully open. Shape: cup-shaped. Color (in course of opening): Upper side: inner petals commonly are near Yellow Group 10D to Yellow Group 11D, and the external petals commonly are near Yellow Group 10D to Yellow Group 11D suffused and edged with near Red Group 42B and 42C and near Orange-Red Group 33A, with a spot at the base near Yellow Group 9A. Underside: near Yellow-Group 10D to Yellow Group 11D suffused with near Red Group 42B and Red Group 42C and near Orange-Red Group 33A, with a spot of near Yellow Group 9A at the base. Color (when open): Upper side: inner petals commonly are near Yellow Group 11D, and the external petals are near Yellow Group 11D amply suffused and edged with near Red Group 42C, with a spot of Yellow Group 11D at the base. Underside: inner petals commonly are near Yellow Group 11D, and the external petals are near Yellow Group 11D amply suffused and edged with near Red Group 42C, with a spot of near Yellow Group 9A at the base. 28D. Fragrance: medium intensity. Petal number: commonly approximately 41 to 43 on average under normal growing conditions. Petal shape: commonly display a rounded tip generally with weak incision and an obtuse base. Petal arrangement: imbricated and commonly without petaloids. Petal texture: firm and leathery. Petal length: commonly approximately 4 to 5 cm on average. Petal width: commonly approximately 5 cm on average. Petal drop: good with the petals commonly detaching cleanly before drying. Stamen number: commonly approximately 148 on average. Anthers: arranged regularly around the styles, commonly approximately 2 mm in size on average, and near Yellow-Orange Group 21D in coloration. Filaments: commonly approximately 4 to 6 mm in length on average, and near Red Group 44B in coloration. Pistils: commonly approximately 98 on average. Styles: commonly approximately 3 mm in size on average, and near Orange-Red Group 34A and 34D in coloration. Stigmas: commonly approximately 1 mm in size and near Orange-Red Group 34A in coloration.

*Receptacle*.—Length: commonly approximately 8 mm on average. Width: commonly approximately 16 mm on average at widest point. Shape: funnel-shaped. Texture: smooth. Color: near Yellow-Green Group 146B to 146D. Fruit formation: very slight with seed formation appearing to be influenced by the climatic conditions that are experienced. Hips: generally cone-shaped with a flattened top and commonly near Yellow-Green Group 147D in coloration.

*Sepals*.—Length: commonly approximately 2.7 cm on average. Width: commonly approximately 1.2 cm on average at the widest point. Shape: lacking a longish point and rounded at the base. Texture: tomentose on the upper surface and smooth on the under surface. Color: commonly near Yellow-Green Group 148C to 148D on the upper surface and near Yellow-Green Group 144B to 144D on the under surface.

*Peduncle*.—Length: commonly approximately 5.5 cm on average. Width: commonly approximately 5 mm on average. Texture: smooth. Color: near Yellow-Green Group 146C.

Development:

*Vegetation*.—Very strong.

*Blooming*.—Medium season, very abundant and substantially continuous.

*Tolerance to diseases*.—Good, with a light sensitivity to black spot (i.e., *Diplocarpon rosae*), sometimes known as Marsonia, during observations to date.

I claim:

1. A new and distinct Grandiflora rose plant characterized by the following characteristics:

(a) forms very strong vegetation, (b) exhibits a semi-erect growth habit with dense dark green foliage having a glossy upper surface, (c) abundantly and substantially continuously forms attractive very double multi-colored cup-shaped blossoms having a medium fragrance, (d) grows well on its own roots, and (e) is well suited for providing distinctive colorful ornamentation in the landscape;

substantially as shown and described.

* * * * *